United States Patent
Huffman

(10) Patent No.: US 8,309,616 B2
(45) Date of Patent: Nov. 13, 2012

(54) INCORPORATION OF CATALYTIC DEHYDROGENATION INTO FISCHER-TROPSCH SYNTHESIS TO SIGNIFICANTLY REDUCE CARBON DIOXIDE EMISSIONS

(75) Inventor: Gerald P. Huffman, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 13/299,862

(22) Filed: Nov. 18, 2011

(65) Prior Publication Data

US 2012/0065278 A1    Mar. 15, 2012

Related U.S. Application Data

(63) Continuation-in-part of application No. 12/790,353, filed on May 28, 2010.

(51) Int. Cl.
*C07C 27/00* (2006.01)

(52) U.S. Cl. ........ 518/700; 518/702; 518/703; 518/705; 518/714; 518/715

(58) Field of Classification Search .......... 518/700, 518/702, 703, 705, 714, 715
See application file for complete search history.

(56) References Cited

U.S. PATENT DOCUMENTS

| | | |
|---|---|---|
| 5,834,522 A | 11/1998 | Mignard et al. |
| 6,392,109 B1 | 5/2002 | O'Rear et al. |
| 6,432,866 B1 | 8/2002 | Tennent et al. |
| 6,713,519 B2 | 3/2004 | Wang et al. |
| 6,872,753 B2 | 3/2005 | Landis et al. |
| 6,875,417 B1 | 4/2005 | Shah et al. |
| 6,903,139 B2 | 6/2005 | Landis et al. |
| 6,919,062 B1 | 7/2005 | Vasileiadis et al. |
| 6,958,363 B2 | 10/2005 | Espinoza et al. |
| 7,012,102 B2 | 3/2006 | Font Freide et al. |
| 7,057,081 B2 | 6/2006 | Allison et al. |
| 7,332,147 B2 | 2/2008 | Takahashi et al. |
| 7,375,142 B2 | 5/2008 | Pearson |
| 2004/0132837 A1* | 7/2004 | Font Freide et al. ......... 518/726 |

* cited by examiner

*Primary Examiner* — Jafar Parsa
(74) *Attorney, Agent, or Firm* — King & Schickli, PLLC

(57) ABSTRACT

A new method of producing liquid transportation fuels from coal and other hydrocarbons that significantly reduces carbon dioxide emissions by combining Fischer-Tropsch synthesis with catalytic dehydrogenation is claimed. Catalytic dehydrogenation (CDH) of the gaseous products (C1-C4) of Fischer-Tropsch synthesis (FTS) can produce large quantities of hydrogen while converting the carbon to multi-walled carbon nanotubes (MWCNT). Incorporation of CDH into a FTS-CDH plant converting coal to liquid fuels can eliminate all or most of the $CO_2$ emissions from the water-gas shift (WGS) reaction that is currently used to elevate the $H_2$ level of coal-derived syngas for FTS. Additionally, the FTS-CDH process saves large amounts of water used by the WGS reaction and produces a valuable by-product, MWCNT.

12 Claims, 3 Drawing Sheets

INCORPORATION OF CATALYTIC DEHYDROGENATION INTO FISCHER-TROPSCH SYNTHESIS TO SIGNIFICANTLY REDUCE CARBON DIOXIDE EMISSIONS

This application is a continuation-in-part of U.S. patent application Ser. No. 12/790,353 filed on 28 May 2010 the entire disclosure of which is incorporated herein by reference.

This invention was made with government support under contract DE-FC26-05NT42456 awarded by US Department of Energy. The government has certain rights in the invention.

TECHNICAL FIELD

The present invention relates generally to the production of synthetic fuels and, more particularly, to a modified and improved Fischer-Tropsch reaction that more economically produces useful synthetic hydrocarbon fuels in a more environmentally acceptable manner by significantly reducing carbon dioxide emissions during the Fischer-Tropsch synthesis process.

BACKGROUND OF THE INVENTION

The Fischer-Tropsch synthesis (FTS) process converts synthesis gas or syngas, a mixture of carbon monoxide and hydrogen, into liquid and gaseous hydrocarbon fuels. The syngas is produced by the gasification of coal, biomass, and other solid hydrocarbons in oxygen and steam at high temperatures and pressures. Typically, coal constitutes 75-100% of the gasification feedstock. The primary products of FTS are normally clean, high quality transportation fuels, including gasoline, jet fuel, and diesel fuel. The synthetic fuels resulting from the FTS process advantageously increase energy diversity. They also burn cleanly and thus hold the promise of improved environmental performance.

Currently there is greatly renewed interest in large scale development of FTS plants to convert coal, biomass, and other hydrocarbon feed stocks into liquid fuels. While state of the art FTS processes produce a very clean fuel, they also produce significant emissions of carbon dioxide, a greenhouse gas. This is because coal-derived syngas typically only has hydrogen to carbon monoxide ($H_2/CO$) molar ratios in the range of approximately 0.6 to 1.1, dependent on the method of gasification. In order to produce liquid fuels by FTS, the $H_2/CO$ ratios of the syngas must be raised to values of 2.0 or higher.

State of the Art FTS technology relies on the water-gas shift (WGS) reaction, $$CO + H_2O \rightarrow CO_2 + H_2,$$

to raise the $H_2/CO$ ratio of the syngas to the required, values of 2.0 or higher. This reaction, unfortunately, produces one $CO_2$ molecule for each $H_2$ molecule it adds to the syngas. Unless the $CO_2$ produced by the WGS reaction during the FTS process is captured and stored, for example, underground, state of the art FTS processes emit this $CO_2$ to the atmosphere, thereby increasing the greenhouse effect. Current technology is focused on preventing this undesirable result by capture and storage of the $CO_2$. Systems for the capture and storage of $CO_2$, including proposed underground storage systems, are, unfortunately, quite expensive, largely untested, and add significant cost and complexity to the production of liquid transportation fuels by FTS.

The present invention relates to a modified and improved FTS process wherein the $H_2$ required to increase the $H_2/CO$ ratio of the syngas to 2.0 or higher is produced by catalytic dehydrogenation (CDH) of the C1-C4 hydrocarbon products of FTS ($C_nH_{2n+2}$ (n=1 to 4) and $C_nH_{2n}$ (n=2 to 4)). Conveniently, these hydrocarbons are gases at ambient conditions of temperature and pressure. CDH converts the C1-C4 products into $H_2$ and multi-walled carbon nanotubes (MWCNT), a valuable by-product, with no production of $CO_2$. Thus, the present invention represents a significant advance in the art allowing for a more environmentally friendly manufacture of liquid transportation fuels from coal and other solid hydrocarbons as an alternative fuel supply, together with a valuable by-product.

SUMMARY OF THE INVENTION

In accordance with the purposes of the present invention as described herein, an improved method is provided of producing liquid transportation fuels from coal and other hydrocarbons. That method comprises the steps of gasifying the coal and other hydrocarbons to produce a synthetic gas (syngas, a mixture of $H_2$ and CO), subjecting that syngas to Fischer-Tropsch synthesis (FTS) to produce a hydrocarbon product stream, and separating that hydrocarbon product stream into C1-C4 hydrocarbons and C5+ hydrocarbons. The C1-C4 hydrocarbons are subjected to CDH to produce $H_2$, which is used to increase the $H_2/CO$ ratio of the syngas to 2.0 or higher, and a valuable by-product, MWCNT. Advantageously, the $H_2$ is produced with no production of $CO_2$. The C5+ hydrocarbons are separately processed into high quality liquid transportation fuels.

In accordance with yet another aspect of the present invention a liquid fuel production facility is provided (FIG. 1). The liquid fuel production facility comprises:
  (1) A gasification unit, 12, to produce syngas from coal or coal+other hydrocarbons.
  (2) A Fischer-Tropsch synthesis (FTS) unit, 14, downstream of the gasification unit.
  (3) A separation unit, 16, downstream from said FTS unit.
  (4) A catalytic dehydrogenation (CDH) unit, 18, downstream from the separation unit to produce $H_2$ and MWCNT from the C1-C4 hydrocarbons.
  (5) A mixing unit, 20, downstream from the gasification unit and upstream from the FTS unit to mix syngas from the gasification unit with $H_2$ from the CDH unit.
  (6) A MWCNT cleaning and catalyst recovery unit, 22, downstream from the CDH unit.

A simple schematic diagram of the Fischer-Tropsch synthesis-Catalytic Dehydrogenation (FTS-CDH) process is shown in FIG. 1. As it will be realized, the method and production facility are capable of other different embodiments and their several details are capable of modification in various, obvious aspects. Accordingly, the drawings and descriptions should be regarded as illustrative in nature and not as restrictive.

BRIEF DESCRIPTION OF THE DRAWINGS

The accompanying drawings incorporated herein and forming a part of the specification illustrate several aspects of the method and production facility. Together with the written description, they serve to explain certain principles of the invention. The drawings included are listed below.

Reference will now be made in detail to the present preferred embodiment of the method and production facility illustrated in the accompanying drawings.

DETAILED DESCRIPTION OF THE PREFERRED EMBODIMENTS OF THE INVENTION

Figure 1:
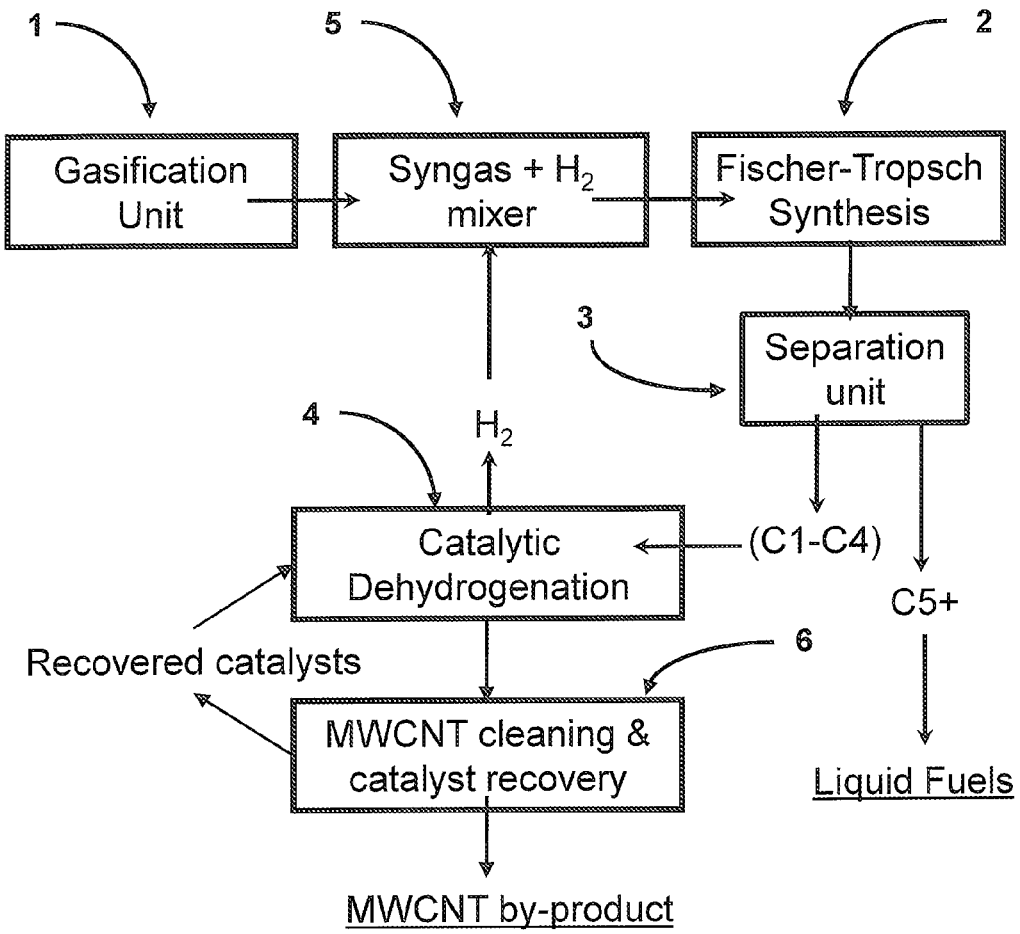
FIG. 1 is a schematic block diagram illustrating the liquid fuel production facility of the present invention.

Reference is now made to FIG. 1 schematically illustrating a liquid fuel production facility 10 for performing the method of the present invention. The liquid fuel production facility 10 comprises: (a) a gasification unit 12; (b) a Fischer-Tropsch Synthesis (FTS) unit 14 downstream from the gasification unit 12; (c) a hydrocarbon separation unit 16 downstream from the FTS unit 14; (d) a catalytic dehydrogenation unit 18 downstream from the separation unit 16; (e) a mixing unit 20 downstream from the gasification unit 12 and the catalytic dehydrogenation unit 18, which mixes $H_2$ from the CDH unit with syngas from the gasification unit to increase the $H_2/CO$ ratio of the syngas entering the FTS unit 14; and (f) a MWCNT cleaning and catalyst recovery unit 22.

More specifically, the feed stock to the gasification unit 12 in FIG. 1 is not limited to coal but may include biomass (such as switchgrass, corn stover, agricultural wastes, lawn wastes, woody biomass wastes from lumbering, and waste products from paper production) and waste hydrocarbons such as waste plastics and rubber products. All of these feedstocks can be gasified at a relatively high temperature and pressure to produce a syngas consisting primarily of CO and $H_2$, which is directed to the FTS unit 14. The FTS hydrocarbon product stream is separated into C1-C4 hydrocarbons and C5+ hydrocarbons in the separation unit 16, which may be a simple condensation apparatus that cools both the C1-C4 and C5+ FTS products to room temperature or slightly lower. At room temperature, all of the C1-C4 FTS products are gases, while all of the FTS C5+ products, which are primarily n-alkanes and n-alkenes, are liquids. The boiling points of the C1-C4 products range from −263.2° F. (−164.0° C.) for methane to 31.1° F. (−0.5° C.) for butane. The lowest boiling point for the C5+ FTS products is that of pentane, 97.2° F. (36.2° C.). Therefore, the C1-C4 products can therefore be easily separated by condensation of the C5+ products at room temperature or slightly below ((~68-77° F.) or (~20-25° C.)).

The un-reacted $H_2$ and CO have much lower boiling points than the C1-C4 products and they will also be separated from the C5+ products by the condensation unit. In a large plant, it might be desirable to further separate the un-reacted $H_2$ and CO from the C1-C4 products by an adsorptive method such as pressure swing adsorption (PSA) before they enter the CDH unit 18 and direct them back to the syngas stream before it enters the FTS unit 14 (see FIG. 1). However, this separation is considered optional since $H_2$ and CO do not undergo any significant reactions in the CDH unit 18.

The $C_{5+}$ hydrocarbons are then processed into liquid fuels such as gasoline, diesel fuel and jet fuel. In contrast, the C1-C4 hydrocarbon product stream is delivered to the catalytic dehydrogenation unit 18, where it is subjected to CDH to produce $H_2$ and multi-walled carbon nanotubes (MWCNT). Advantageously, the $H_2$ is added to the syngas in the mixing unit 20 in order to increase the $H_2/CO$ ratio to desired levels for FTS processing. Concurrently, the carbon nanotubes are delivered to the MWCNT cleaning and catalyst recovery unit 22. There, the MWCNT are cleaned in a dilute nitric acid solution in order to dissolve the catalyst. This produces clean MWCNT that are approximately 99.5% carbon and can be removed from the solution by, for example, centrifugation or filtration. The catalyst can then be recovered from the cleaning solution by adding appropriate bases to precipitate it, for example, in the form of metallic oxides or oxyhydroxides. These recovered catalysts can ultimately be recycled to the catalytic dehydrogenation unit 18, where they are quickly returned to their active metallic form by reduction in the reducing atmosphere of the CDH unit. The cleaned MWCNT can be sold on the market and used to create other products.

Any known method of gasification may be used in the FTS-CDH process. However, methods of gasification that produce a $H_2/CO$ ratio for the coal-derived syngas $\geq 0.8$ are preferred. Of course, it is known in the art that the ratio may vary greatly from, for example, 0.6 to 1.1, depending on the method of gasification and the composition of the oxidizing gas, which is normally a mixture of oxygen or air and steam.

The current method may also use any known method for FTS processing. Currently, the fixed-bed tubular reactor (FBTR) is favored by Sasol, the South African company that leads the world in the commercial development of FTS liquid transportation fuel production. No matter which FTS processing method is used, it is beneficial to complete the FTS processing at temperatures of approximately 200-300° C. using a Co-based FTS catalyst in order to produce fairly high yields of C1-C4 product. Fe-based FTS catalysts are not used in the FTS-CDH process because Fe is an excellent catalyst for the water-gas shift (WGS) reaction, which produces carbon dioxide.

The separation of the C1-C4 product stream from the C5+ product stream may be accomplished by condensation of the C5+ products, which are primarily n-alkanes and n-alkenes, and have significantly higher boiling points than the C1-C4 products. As discussed earlier, all C5+ FTS products are liquids and all C1-C4 FTS products are gases at room temperature, making separation by condensation relatively easy.

With respect to catalytic dehydrogenation of the C1-C4 production stream, any catalytic dehydrogenation process in which the catalysts exhibit relatively long lifetimes (~20 hours or more) and high $H_2$ yields (~60 to 80%) can be used. One particularly useful catalytic dehydrogenation (CDH) process is disclosed in issued U.S. Pat. No. 6,875,417, the full disclosure of which is incorporated herein by reference. This catalytic dehydrogenation process includes the step of passing the C1-C4 hydrocarbons over a catalyst comprising a binary Fe-based alloy catalyst on one of several types of supports. Fe-alloy catalysts that have been successfully tested to date include Fe—Ni, Fe—Mo, Fe—Pd, and Fe—Mn. Supports that have been successfully utilized to date include $\gamma$-$Al_2O_3$, high surface area $SiO_2$, a basic support —Mg(Al)O, and carbon nanotubes (MWCNT). Basic supports have the advantage that cleaning the carbon nanotubes is more easily accomplished because basic supports are easily dissolved in a dilute acid solution. Typically, processing temperatures for CDH range from about 400° C. to about 900° C. with a preferred temperature range of about 600 to 800° C.

CDH catalyst preparation: binary metal-ferrihydrites containing iron and a secondary element, M, selected from a group of metals consisting of Ni, Mo, Mn, Pd, V, Cr, Co, Zn, W and any mixtures thereof, are deposited on the support by an incipient wetness method. Fe and the secondary metal M are present in approximately a composition ratio of 2-4 parts Fe to 1 part M and are included in a ratio of between 5.0 to 20.0 weight percent with respect to the support substrate. In their active state, the Fe-M catalysts are reduced either in hydrogen or syngas to an Fe-M-C metal alloy. A face-centered austenitic metal alloy appears to be the most active catalytic phase, although martensitic alloy forms are also present and probably active for CDH. The preferred temperature range for catalyst reduction is about 600 to 800° C. and can be quickly accomplished in the strongly reducing atmosphere of the CDH reactor.

Energy Requirements

Our research has established that CDH at temperatures in the range of 600 to 800° C. converts $CH_4$ to $H_2$ and MWCNT and C2-C4 hydrocarbons (ethane, propane, etc.) into $CH_4$, $H_2$, and MWCNT using the Fe-alloy catalysts described above, the least expensive of which are Fe—Ni and Fe—Mn. Moreover, the only gases detected during CDH of C2-C4 hydrocarbons at temperatures $\geq 600°$ C., are $CH_4$ and $H_2$. Therefore, the reaction of primary interest for energy requirements is CDH of methane to produce $H_2$ and MWCNT at temperatures of 600-800° C. (923-1073 K), with an optimum CDH temperature of approximately 1,000 K (727° C.).

The activation enthalpy for the CDH reaction can be determined using transition state theory (TST). According to TST, the CDH reaction can be considered to be in a state of pseudo-equilibrium. As indicated by Eq. 1 below, the reactant, $CH_4$, is considered to be in pseudo-equilibrium with an activated complex, $[CH_4^\ddagger]$, on the catalyst surface. At a given temperature, as the bonds of the activated complex break to form $H_2$ and solid carbon in the form of MWCNT, fresh methane is supplied to maintain the activated complex in a state of pseudo-equilibrium. This pseudo-equilibrium reaction is expressed in the form below.

$$CH_4 \leftrightarrows [CH_4^\ddagger] \rightarrow C_{MWCNT} + 2H_2 \quad (1)$$

The rate constant (v) for this reaction at temperature T can be written as $$v=(k_B T/h) \cdot K^\ddagger_p(T)=(k_B T/h) \cdot \exp(-\Delta G^\ddagger/RT)=(k_B T/h) \cdot \exp(-\Delta H^\ddagger/RT+\Delta S^\ddagger/R), \quad (2)$$

where $k_B$ and h are the Boltzmann and Planck constants, respectively, $k_B T/h$ is a fundamental frequency and $K^\ddagger_p(T)$ is the pseudo-equilibrium constant. $\Delta G^\ddagger$, $\Delta H^\ddagger$, and $\Delta S^\ddagger$ are the "activation free energy", "activation enthalpy" and "activation entropy" of the reaction, respectively. From Eq. 1, the rate constant can also be written in terms of the mole fractions of $H_2$ and $CH_4$ as $$v=(k_B T/h) \cdot (H_2)^2/(CH_4) \quad (3)$$

This gives $$\ln\{K^\ddagger_p(T)\}=\ln\{(H_2)^2/(CH_4)\}=-\Delta H^\ddagger/RT+\Delta S^\ddagger/R \quad (4)$$

Figure 2:
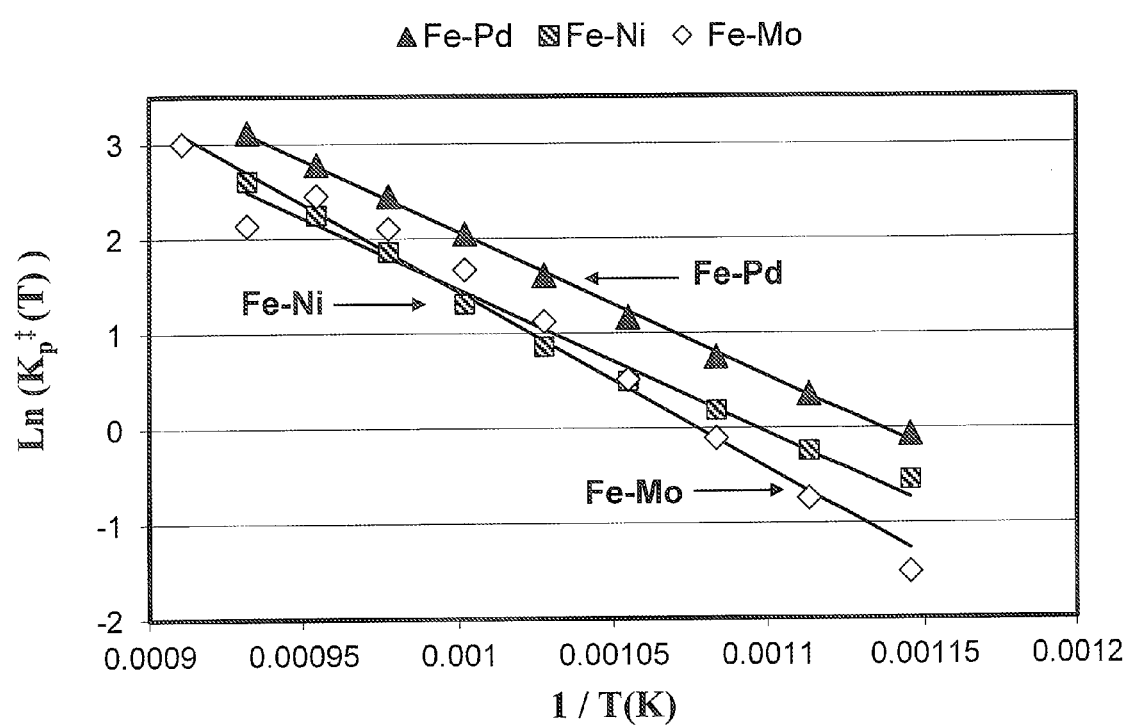
FIG. 2 shows linear plots of 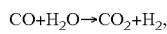 $\ln(K^{\ddagger}_p(T))$ vs 1/T used to determine $\Delta H^{\ddagger}$ and $\Delta S^{\ddagger}$, which are used to calculate the energy balance of the FTS-CDH process.

The slope of the linear plot of $\ln\{(H_2)^2/(CH_4)\}$ vs. $1/T$ then yields the "activation enthalpy" of the catalyzed reaction, ($\Delta H^\ddagger$), while the intercept yields the "activation entropy" ($\Delta S^\ddagger$). The resulting linear plots obtained from our experimental results for three different catalysts (Fe—Ni, Fe—Mo, and Fe—Pd supported on γ-alumina) are shown in FIG. 2 and the values obtained for $\Delta H^\ddagger$ and $\Delta S^\ddagger$ are given in Table 1. The free energies of the reaction ($\Delta G^\ddagger$) at a temperature of 1,000 K (727° C.), a good operating temperature for CDH, are also shown.

TABLE 1

Figure 3:
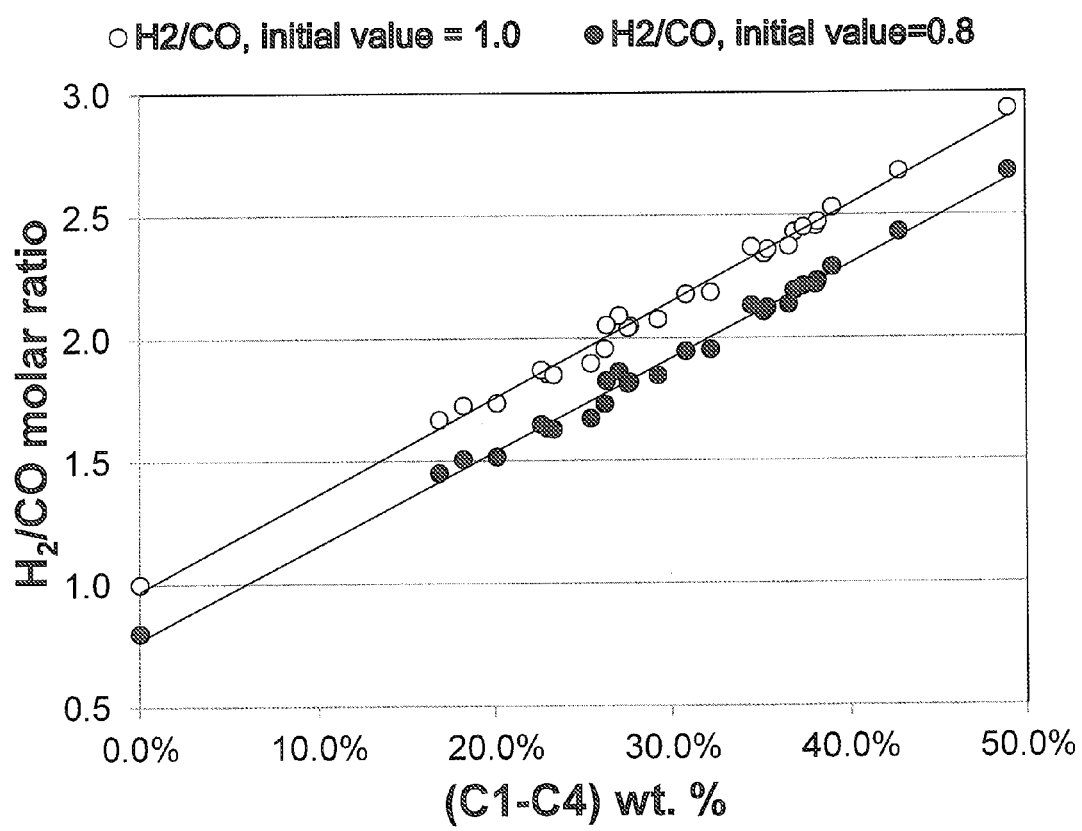
FIG. 3 shows plots of the $H_2/CO$ ratio of the syngas as modified by the CDH process entering the FTS reactor. It is plotted versus the (C1-C4) wt. % for two different initial $H_2/CO$ ratios of the syngas emanating from the gasification unit, 0.8 and 1.0.

Values of $\Delta H^\ddagger$ and $\Delta S^\ddagger$ determined from the slopes and intercepts of the linear plots in FIG. 3 and values of $\Delta G^\ddagger$ at 1,000 K.

| Catalyst | $\Delta H^\ddagger$ (kcal/mol) | $\Delta S^\ddagger$ (cal/mol/K) | $\Delta G^\ddagger$ (kcal/mol) |
|---|---|---|---|
| Fe—Ni/Al$_2$O$_3$ | 30 | 32.9 | −2.9 |
| Fe—Pd/Al$_2$O$_3$ | 30.2 | 34.3 | −4.1 |
| Fe—Mo/Al$_2$O$_3$ | 36.9 | 39.7 | −2.8 |

The "activation enthalpy", $\Delta H^\ddagger$, can be provided by the energy released on cooling the syngas from the gasification temperature (typically ~1,500-1,600 K) to an appropriate operating temperature for the CDH reaction (approximately 1,000 K). This energy can be calculated using enthalpy tables for CO and $H_2$. For a syngas with $H_2/CO=0.8$-1.0, it is found that $H^0(1500$-1600 K$)-H^0(1000$ K$)=-7.86$ to $-9.51$ kcal/mol of syngas. To calculate typical numerical results of the FTS-CDH process with real data, 26 sets of experimental FTS data were selected from the literature. Only FTS data obtained using Co-based catalysts were used, since Co is not a WGS catalyst. For the 26 FTS experimental data sets used in this study, the (C1-C4) products contained an average of 28.7 mol % of the C. Therefore, the average energy available from this source for CDH of the (C1-C4) products is −27.4 to −33.1 kcal/mol, which is close to the values of the activation enthalpy, $\Delta H^\ddagger$, derived from FIG. 2 and shown in Table 2.

Calculations of the Daily Amounts of: (1) $H_2$ Produced and $H_2/CO$ Molar Ratios Achieved; (2) MWCNT Produced; (3) $CO_2$ Emissions Avoided; and (4) Water Saved The 26 FTS experimental data sets obtained using Co-based catalysts that were selected from the literature were also used to calculate the amounts of $H_2$ and MWCNT produced by CDH of the C1-C4 products and the $H_2/CO$ ratios achieved. A brief summary of the equations used is given below.

Summary of Symbols and Equations:

The mole percentages of $H_2$ and CO are denoted simply by $H_2$ and CO. The weight percentages are denoted more specifically by $H_2$ (wt. %) and CO (wt. %).

C1=wt. % methane; $(C2$-$C4)_{par}$=wt. % of paraffins containing 2, 3, or 4 C atoms; and $(C2$-$C4)_{ol}$=wt. % of olefins containing 2, 3, or 4 C atoms $\Delta H_2$(wt. %) and MWCNT(wt. %)=wt. % of $H_2$ and multi-walled carbon nanotubes (MWCNT) produced by CDH of the (C1-C4) products of FTS.

The values of $H_2/CO$ are calculated by equations (5) and (6) for initial values of $H_2/CO=1.0$ or 0.8, respectively.

$$H_2/CO=14*(6.67 \text{ wt. \%}+\Delta H_2(\text{wt. \%})/(100 \text{ wt. \%}-(6.67 \text{ wt. \%}+\Delta H_2(\text{wt. \%})) \quad (5)$$

$$H_2/CO=14*(5.41 \text{ wt. \%}+\Delta H_2(\text{wt. \%})/(100 \text{ wt. \%}-(5.41 \text{ wt. \%}+\Delta H_2(\text{wt. \%})) \quad (6)$$

The 26 FTS data sets taken from the literature to quantify the FTS-CDH concept exhibited an average of 85% paraffins and 15% olefins and an average Anderson-Schulz-Flory (ASF) coupling probability of $\alpha=0.85$. Using these values, the following equations were derived for $\Delta H_2$ and MWCNT.

$$\Delta H_2(\text{wt. \%})=25\% \cdot C1+18.30\% \cdot (C2\text{-}C4)_{par}+14.29\% \cdot (C2\text{-}C4)_{ol} \quad (7)$$

$$MWCNT(\text{wt. \%})=75\% \cdot C1+81.69\%\% \cdot (C2\text{-}C4)_{par}+85.71\%\% \cdot (C2\text{-}C4)_{ol} \quad (8)$$

If the (C2-C4) paraffins and olefins were not given separately in a FTS data set, equations 7 and 8 were averaged to give equations 9 and 10 below.

$$\Delta H_2(\text{wt. \%}) = 25\% \cdot (C1) + 17.70\% \cdot (C2\text{-}C4)_{total} \quad (9)$$

$$MWCNT(\text{wt. \%}) = 75\% \cdot (C1) + 82.29\% \cdot (C2\text{-}C4)_{total} \quad (10)$$

Equations (5) and (6) were used to calculate $H_2/CO$ and equations (7), (8), (9), and (10) were used to calculate $\Delta H_2$ (wt. %) and MWCNT(wt. %). The results are summarized in FIG. 3 and Table 2. In FIG. 3, it is seen that the $H_2/CO$ molar ratio increases linearly with the wt. % of C1-C4. For an initial $H_2/CO$ ratio of 1.0, the $H_2/CO$ ratio is increased to $\geq 2.0$ for 19 of the experimental FTS data sets examined and to $\geq 1.7$ for all 26 data sets. For an initial $H_2/CO$ ratio of 0.8, 13 of the 26 FTS data sets examined have their $H_2/CO$ increased to $\geq 2.0$ and all 26 to $\geq 1.5$. More detailed numerical results are shown for several of the 26 FTS data sets in Table 2, selected to be well-distributed over the whole data range. In Table 2, the $\Delta H_2$ and MWCNT percentages and $H_2/CO$ values have been applied to the example of a 50,000 barrel/day (bbl/day) FTS-CDH plant to estimate the amounts of hydrogen and MWCNT produced and $CO_2$ emissions avoided relative to a standard FTS plant. The latter calculations are relatively simple and will not be repeated here. They assume that the density of oil is 825 kg/m³, which is typical of premium light crude oils and gives a weight per barrel (42 gallons) of 131.2 kg.

The last column of Table 2 shows the average values for all 26 FTS data sets. They indicate that on average, for a 50,000 bbl/day plant, the FTS-CDH process will avoid the emission of over 16,000 tons/day of $CO_2$ emissions and save nearly 1.6 million gallons/day of water, while producing over 3,200 tons/day of MWCNT, a valuable by-product.

There are many possible applications that could utilize large amounts of MWCNT. These include:

Removal of toxic metals from water.

Use of MWCNT in fire-retardant coatings.

Ultra-strong MWCNT fibers and ropes for use in transmission lines and cables.

Replacement of carbon black in tires by MWCNT to improve their strength, elasticity, and durability.

High-strength, high ductility, lightweight MWCNT-polymer composites for use as structural materials in automobiles and trucks, military vehicles, airplanes, body and vehicle armor, and sports (baseball, football, golf, etc.).

The last of these applications would seem to hold the most promise. Governments may soon mandate lighter, stronger vehicles to increase mileage rates and decrease $CO_2$ emissions without endangering passengers. Utilization of carbon fiber re-enforced plastic components of racing cars is already common practice. Currently, over 16 million cars and trucks are produced annually in the U.S. alone. If only 100 lbs. of MWCNT were required per vehicle, this alone could utilize all of the MWCNT output per year of a 50,000 bbl/day FTS-CDH plant. Utilization of MWCNT in tires is another obvious large-scale vehicular application of MWCNT. Although it is pre-mature to attempt any serious economic analysis of the FTS-CDH process, it is worth noting that a price of only $1.00 per pound of MWCNT could yield approximately $3.2 million per day for a 50,000 bbl/day FTS-CDH plant. This would be comparable to the revenue from the oil.

TABLE 2

Typical results for the weight percentages and amounts per day of MWCNT and $H_2$ produced per day, the $H_2/CO$ ratios achieved, the $H_2O$ saved, and the $CO_2$ emissions avoided for a 50,000 bbl/day FTS-CDH plant.

| Item reported | | | | | | Average |
|---|---|---|---|---|---|---|
| C1-C4 (wt. %) | 16.80% | 23.30% | 29.20% | 35.40% | 39.00% | 30.74% |
| $\Delta H_2$(wt. %) | 4.05% | 5.24% | 6.55% | 8.06% | 8.98% | 7.03% |
| MWCNT(wt. %) | 12.77% | 18.06% | 22.65% | 27.42% | 30.11% | 23.74% |
| $\Delta$ MWCNT (tons) | 1,460 | 2,196 | 2,982 | 3,962 | 4,622 | 3,209 |
| $\Delta H_2$ (tons) | 352 | 494 | 669 | 902 | 1,064 | 734 |
| *$H_2/CO$ (mol ratio) | 1.68 | 1.89 | 2.13 | 2.42 | 2.60 | 2.23 |
| **$H_2/CO$(mol ratio) | 1.46 | 1.67 | 1.90 | 2.18 | 2.35 | 2.00 |
| $H_2O$ saved (gal) | 759,841 | 1,067,071 | 1,444,859 | 1,947,424 | 2,297,997 | 1,584,387 |
| $CO_2$ avoided (tons) | 7,740 | 10,870 | 14,718 | 19,837 | 23,408 | 16,139 |

*Initial value of $H_2/CO$ = 1.0;
**Initial value of $H_2/CO$ = 0.8

In summary, catalytic dehydrogenation (CDH) of the gaseous products (C1-C4) of Fisher-Tropsch synthesis (FTS) can produce large quantities of hydrogen while converting the carbon to multi-walled carbon nanotubes (MWCNT). Incorporation of CDH into a FTS-CDH plant converting coal to liquid fuels could eliminate all or most of the $CO_2$ emissions from the WGS reaction that is currently used to elevate the $H_2$ level of coal-derived syngas for FTS. For most of the experimental FTS data we examined, the calculated $H_2/CO$ ratios for a FTS-CDH plant indicated that CDH could virtually eliminate the need for the WGS. For an average 50,000 barrel/day FTS-CDH plant, this would avoid emissions of approximately 16,000 tons/day of $CO_2$, save over 1.5 million gallons/day of water, and produce over 3,000 tons/day of a valuable by-product, multi-walled carbon nanotubes. Perhaps most advantageously, it would avoid the expensive and uncertain procedure of capturing and sequestering approximately 16,000 tons/day of $CO_2$.

What is claimed:

1. A method of producing liquid fuels from coal or coal+biomass or other solid hydrocarbons, comprising:

Gasifying a starting material selected from a group consisting of coal, biomass, waste hydrocarbons, and mixtures thereof to produce a syngas;

Subjecting said syngas to Fischer-Tropsch synthesis (FTS) to produce a hydrocarbon product stream;

Separating said hydrocarbon product stream into C1-C4 hydrocarbons and C5+hydrocarbons that are used as liquid fuels;

Subjecting said C1-C4 hydrocarbons to catalytic dehydrogenation (CDH) in the presence of a catalyst to produce hydrogen ($H_2$) and multi-walled carbon nanotubes (MWCNT);

Utilizing energy released in cooling the syngas from a gasification temperature of between about 1,500-1,600° K to a useful operating temperature for the CDH reaction of about 1,000° K to provide the activation enthalpy required for catalytic dehydrogenation;

Mixing said $H_2$ with the syngas from said gasifier to increase the $H_2$/CO ratio of the syngas for FTS to 2.0 or higher thereby enabling production of liquid fuels by combined FTS and CDH with significantly reduced $CO_2$ emissions relative to conventional FTS processing;

Cleaning said MWCNT and dissolving said CDH catalyst in a cleaning solution;

Recovering the MWCNT from the cleaning solution by centrifugation, filtration, or other techniques;

Recovering said catalyst from the resulting cleaning solution by standard precipitation methods and recycling it to the CDH reactor.

2. The method of claim 1 including using dilute nitric acid as said cleaning solution, recovering said catalyst from said cleaning solution, and recycling said catalyst.

3. The method of claim 1 including using a starting material comprising between about 50 and 100 weight percent coal, between about 0 and about 50 weight percent biomass and/or between about 0 and about 50 weight percent of waste hydrocarbons, including plastics and rubber products.

4. The method of claim 1 including selecting said biomass from a group of materials consisting of switchgrass, corn stover, agricultural wastes, lawn wastes, woody biomass from lumbering wastes, and waste products from paper production.

5. The method of claim 1, including subjecting said syngas to FTS at temperatures in the approximate range of 220-300° C. in the presence of a Co-based FTS catalyst.

6. The method of claim 1, wherein said separation is accomplished by condensation.

7. The method of claim 1, wherein said catalytic dehydrogenation includes passing said (C1-C4) hydrocarbons over a catalyst comprising a binary metallic iron-based alloy, Fe-M, where the secondary metal M may be selected from a group consisting of Ni, Mo, Mn, Pd, V, Cr, Co, Zn, W and any mixtures thereof.

8. The method of claim 7, including using an Fe/M alloy ratio in a range of 1-4.

9. The method of claim 8 including depositing said Fe/M alloy on a support.

10. The method of claim 9 including selecting said support from a material selected from a group consisting of $Al_2O_3$, $SiO_2$, $Mg_5AlO$, $MgO$, and multi-walled carbon nanotubes (MWCNT).

11. The method of claim 10, including reducing said Fe/M catalysts to their active metallic state, either in hydrogen or syngas; an austenitic metallic alloy is preferred but other metallic structures can also achieve catalytic dehydrogenation.

12. A liquid fuel production facility, comprising:

a gasification unit to produce a syngas from a starting material selected from a group consisting of coal, biomass, waste hydrocarbons, waste carbon and mixtures thereof;

a Fischer-Tropsch unit downstream from said gasification unit to produce a hydrocarbon product stream from said syngas, said hydrocarbon product stream including C1-C4 hydrocarbons and C5+ hydrocarbons used as liquid fuels;

a separation unit between said Fischer-Tropsch unit and said catalytic dehydrogenation unit to separate said hydrocarbon product stream into C1-C4 hydrocarbons and $C_5^+$ hydrocarbons used as liquid fuels;

a catalytic dehydrogenation unit downstream from said separator unit to produce hydrogen gas and carbon nanotubes from said C1-C4 hydrocarbons;

a mixing unit downstream from the gasifier and the catalytic dehydrogenation unit which uniformly mixes hydrogen from the CDH unit and syngas from the gasification unit to produce modified syngas with significantly enhanced $[H_2]/[CO]$ ratios; and a MWCNT cleaning and catalyst recovery unit.

* * * * *